United States Patent [19]

Cornwell

[11] Patent Number: 5,195,635
[45] Date of Patent: Mar. 23, 1993

[54] CRYPTOPLATE MOBILE SYSTEM FOR DISPOSING AND CONTAINING SHARPS AND INFECTIOUS MEDICAL WASTES

[75] Inventor: James T. Cornwell, Cleveland, Tenn.

[73] Assignee: Quality Containers International, Inc., Cleveland, Tenn.

[21] Appl. No.: 833,075

[22] Filed: Feb. 10, 1992

[51] Int. Cl.$^5$ .............................................. B65D 85/24
[52] U.S. Cl. .................................... 206/366; 206/370; 220/409; 280/47.34
[58] Field of Search ............... 206/365, 366, 370, 438; 220/908–910; 280/47.34

[56] References Cited

U.S. PATENT DOCUMENTS

| | | |
|---|---|---|
| 4,520,926 | 6/1985 | Nelson . |
| 4,576,281 | 3/1986 | Kirksey ................................ 206/366 |
| 4,662,516 | 5/1987 | Baker, Sr. et al. ................... 206/366 |
| 4,736,860 | 4/1988 | Bemis . |
| 4,779,728 | 10/1988 | Hanifl et al. . |
| 4,809,850 | 3/1989 | Laible et al. ......................... 206/366 |
| 4,816,307 | 3/1989 | Honeycutt . |
| 4,828,107 | 5/1989 | Spencer ................................ 206/366 |
| 4,911,294 | 3/1990 | Russo et al. ......................... 206/366 |
| 4,955,496 | 9/1990 | Nelson . |
| 4,972,950 | 11/1990 | Shillington ........................... 206/370 |
| 4,984,686 | 1/1991 | Shillington . |
| 5,040,904 | 8/1991 | Cornwell . |
| 5,097,950 | 3/1992 | Weiss et al. ......................... 206/366 |
| 5,103,997 | 4/1992 | Shillington et al. ................. 206/366 |
| 5,111,958 | 5/1992 | Witthoeft ............................. 220/505 |
| 5,135,144 | 8/1992 | Blakely ................................ 206/366 |

Primary Examiner—Jimmy G. Foster
Attorney, Agent, or Firm—Notaro & Michalos

[57] ABSTRACT

A system for containing sharps and infectious medical wastes generated by Hospitals and all health care facilities comprises a master barier container, a sharps container and a support holder/stand. The system is designed to form a mobile, all in one, container that in turn allows safe disposing and containing of infectious medical wastes, sharp or non sharp.

7 Claims, 3 Drawing Sheets

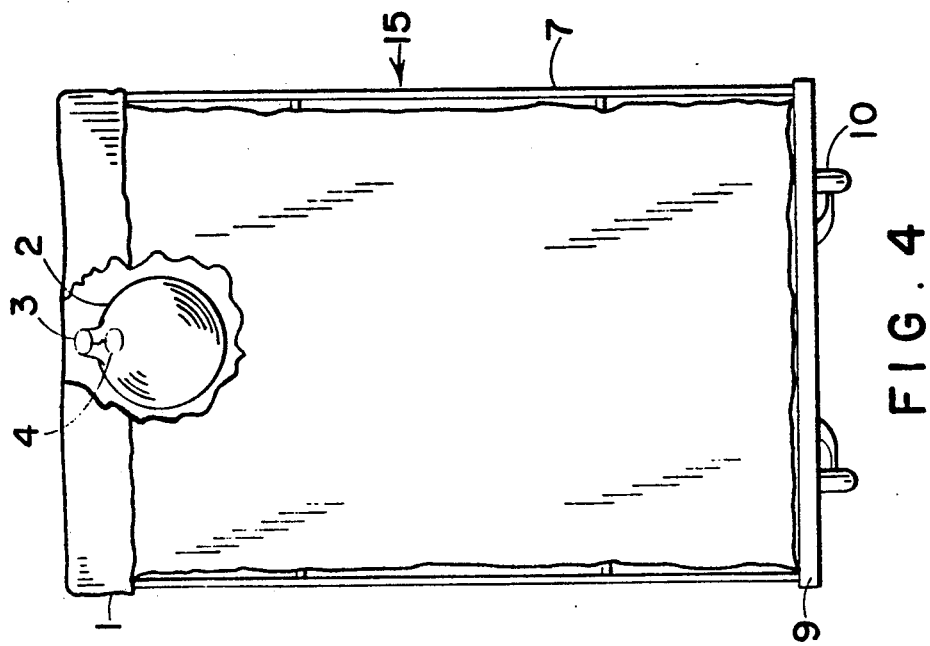
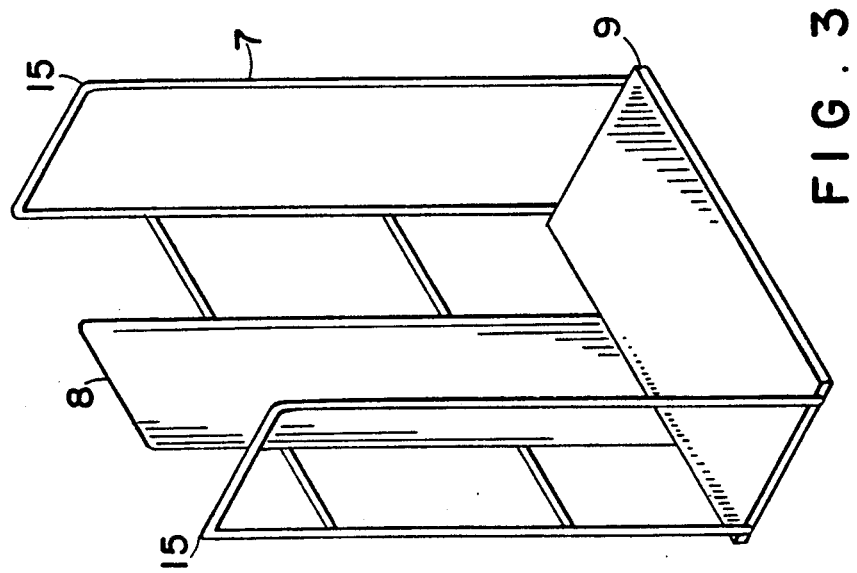

CRYPTOPLATE MOBILE SYSTEM FOR DISPOSING AND CONTAINING SHARPS AND INFECTIOUS MEDICAL WASTES

FIELD AND BACKGROUND OF THE INVENTION

This invention relates to a single system for disposing of and containing, storing, and transporting sharps and infectious medical waste, such as; sharps, liquids, semi-solids, and solids. These wastes are generated by health care institutions including hospitals, health clinics, ambulatory surgical centers, outpatient treatment facilities, nursing homes, dialysis centers, blood banks, medical laboratories and physician's and dentist's office.

This system is comprised of a master barrier container; a sharps container; and a support holder/stand. These three items create a safe method for disposal and containing infectious medical wastes, including bloodborne pathogens. Bloodborne pathogens can cause diseases in humans such as; HEPATITIS B VIRUS (HBV) and HUMAN IMMUNODEFICIENCY VIRUS (HIV) which can cause AIDS, as well as TUBERCULOSIS (TB).

ASSISTANT SECRETARY OF LABOR GERARD F. SCANNWELL stated, "It is vital that we protect workers who put their lives on the line to provide compassionate care for other Americans in illness and emergencies—protecting and saving lives, treating the sick, cleaning rooms and discarding wastes—from the risks of exposure". This statement along with the OCCUPATIONAL SAFETY AND HEALTH ADMINISTRATION'S bloodborne pathogen standards (29CFR PART 1910) identify the necessity for utilizing this invention in preventing the healthcare workers from 9200 infections and 200 deaths per year, that are caused by bloodborne pathogens or other types of infections.

THE JOURNAL OF THE AMERICAN MEDICAL ASSOCIATION's research function estimates that in 1990, all generators of infectious medical wastes produced in excess of 63 million pounds of this wastes. This represents a 47.9 percent increase over the 42.6 million pounds of infectious medical wastes generated by all medical facilities in 1987.

Sharps, including disposable syringes with needles, needles, capillary tubes, scalpels, razors, glass tubing, slides and vials (broken or whole) and other sharp items capable of piercing plastic films, account for 48% of the total weight of medical wastes classified as infectious. 92% of this waste is collected and contained in rigid, puncture proof containers while the remaining 8% is collected and contained in cardboard containers or some other form of puncture proof container.

SUMMARY OF THE INVENTION

This invention is a system for Sharps and waste which includes:

1. A co-extruded flexible master barrier container constructed of a combination of polymers highly resistant to puncture with structural integrity to reduce stress including resistance to rupture upon impact and additional elongation strength to reduce the frequency of tear. This is produced through an extrusion process that forms lay flat tubing in a desired thickness and width.

With a specialized seal of the invention applied transversely to the lower margin of the lay flat tubing, at a desired length, a master barrier container is formed. The tube material has a selected color, is opaque, carries the biohazard symbol and has appropriate wording thereon. The inside layer of the master barrier container is puncture proof and leak proof, and a semi-flexible sharps container is ultrasonically welded thereto.

2. A semi-flexible, puncture proof, leak proof sharps container is ultrasonically welded to the inside back wall of the master barrier container. This sharps container is produced of non-penetrable polymers which contain a colorant for the body of the container on which the biohazard symbol and wording are printed. The sharps container's opening, in which the sharps items are inserted, has a closure which is printed with a bichazard symbol, and than when closed, locks in place, creating a sealed, leak proof closure.

3. A support holder/stand, with casters, provides stability, firmness and resistance to movement by the master barrier container when positioned on the support holder/stand and clamped in place. This support holder/stand is mobile so that it can be moved to the point of collection and containment of the sharps and/or liquid, semi-liquid or solid infectious medical wastes. The master barrier container and the self contained sharps container, when filled to the desired capacity, is closed using a master barrier container closure tape. This closure insures a leak proof top closure for the master barrier container system.

In the container system of the invention was designed and engineered as a single source to dispose, contain, store and transport infectious medical wastes including sharps in one container. With the system positioned on its support stand, which is highly mobile and includes functional casters, the master barrier container can be positioned in one location or moved to and from the closest point of use and practical to the source in which the infectious medical wastes are generated. This, includes sharps and non-sharps infectious medical waste.

Generally, in all medical/health care facilities, the sharps container is located some distance from the location of the non-sharps container. When the medical/health care facility employee disposes of a sharp, the employee goes to the location of the sharps container for insertion of the sharp or to the location of the non-sharps container for insertion of the wastes. When the sharps container is filled, it is then deposited in a color coded, printed plastic biohazard bag for transport to an incinerator. By transporting contaminated medical wastes a distance greater than arms reach, a greater risk of mishap exists.

Non-sharp infected wastes (biological, pathological, blood and blood products, communicable disease waste treatment products, animal cancer wastes, surgery and autopsy wastes, environmental laboratory wastes, dialysis wastes, etc.) are collected and contained in color coded plastic bags that are, printed with biohazard wording and symbols. These bags, due to the thickness of the bag, are generally "double bagged" for added strength. If the bag is used to line a solid walled container such as a can, if the can is not properly cleaned and sterilized, it may can contaminate the outer side of the bag. When the bag is removed from the can it is then placed in another color coded, printed bag, and put into a box prior to transport to a disposal facility. When using the system of the invention with its support holder/stand, there is no contamination of the outside of the master barrier container. Therefore, double bagging is not required.

The master barrier container, a flexible co-extruded combination of polymers, has the special seal of the invention at its lower end. This seal consists of two transverse master seals with 45° angle members therebetween, forming triangles between the upper and lower transverse master seals. The said seal is a fail proof, leak proof barrier. Also, the master barrier container has a closure at the upper lip (open mouth) of the bag, which consists of a length of self adhesive tape. One half of this tape is applied to the back wall of the master barrier container during the manufacturing cycle. The other half of the sealing tape protrudes above the back wall and is protected from its adhesive quality by a removal paper which exposes the adhesive when removed.

The container system that is both the internal sharps container and the master barrier container is filled with one of the following wastes . . .

SHARPS CONTAINER-needles; disposable syringes with needles; capillary tubes; scalpels; glass tubing; slides; vials; and other items capable of puncturing the semi-flexible rigid containers.

MASTER BARRIER CONTAINER-non sharp infectious medical wastes including microbiological, pathological, blood and blood products, communicable disease waste treatment products, animal cancer waste treatment products, contaminated laboratory wastes, dialysis wastes, and other related wastes.

When the system is filled and ready for closure, the internal semi-flexible, puncture proof, leak proof sharps container's lid is closed and locked, and the container is removed from the support stand, and closure tape removal paper is peeled away and the exposed tape with adhesive is folded across the opening of both the stretched together back and front lips of the master barrier container. When pressure across the tape applied to the front lip, and with the tape on the back lip in place, the closure resists leakage or seepage or liquids of any other contents enclosed in the master barrier container, and also creates a safe environment for all infectious medical wastes including sharps.

The polymers, colorants and additives contain no diarylides or heavy metals. Diarylides, when exposed to temperatures in excess of 385° F. release a potential carcinogen, 33DCB. Heavy metals, including cadmium, lead, mercury, chromium or lead chromates release carcinogens when incinerated. Therefore, when the container of the invention is incinerated, it burns clean, releasing no environmentally damaging liquids, gases or vapors. The ash residue is clean.

BRIEF DESCRIPTION OF THE DRAWINGS

FIG. 3 is an isometric view of the support holder/stand.

FIG. 4 illustrates the container system of the invention.

DESCRIPTION OF THE PREFERRED EMBODIMENT

Figure 1:
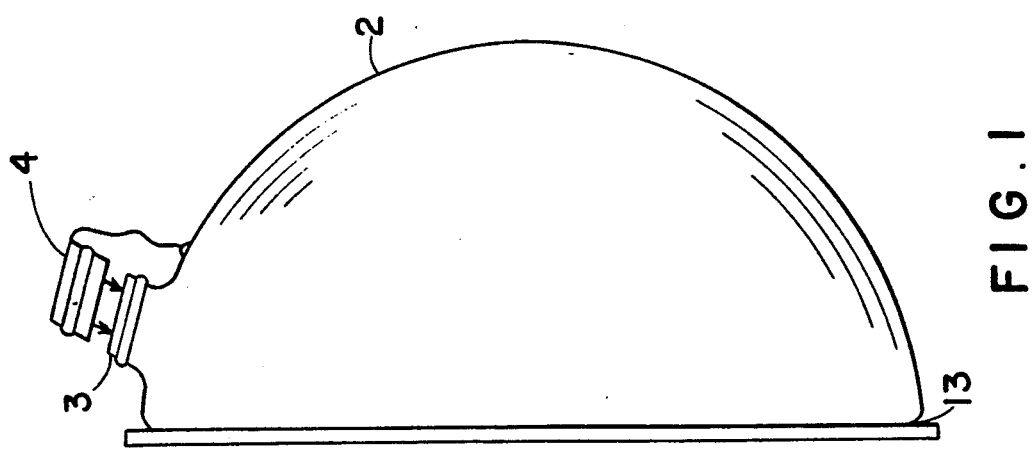
FIG. 1 is a side view of the sharps container, ultrasonically welded to the back wall of the master barrier container.

As shown in FIG. 1 the sharps container 2 has a lid 4 that will be pushed into the neck 3 of the sharps container 2 for a leak proof, closure. Also, in FIG. 3 the illustration shows that the sharps container 2 is attached to the master barrier container 1. This is done by an ultrasonic weld 13. Sharps container 2 has a body with a rounded, bulbous hemispherical front wall and a flat rear wall.

Figure 2:
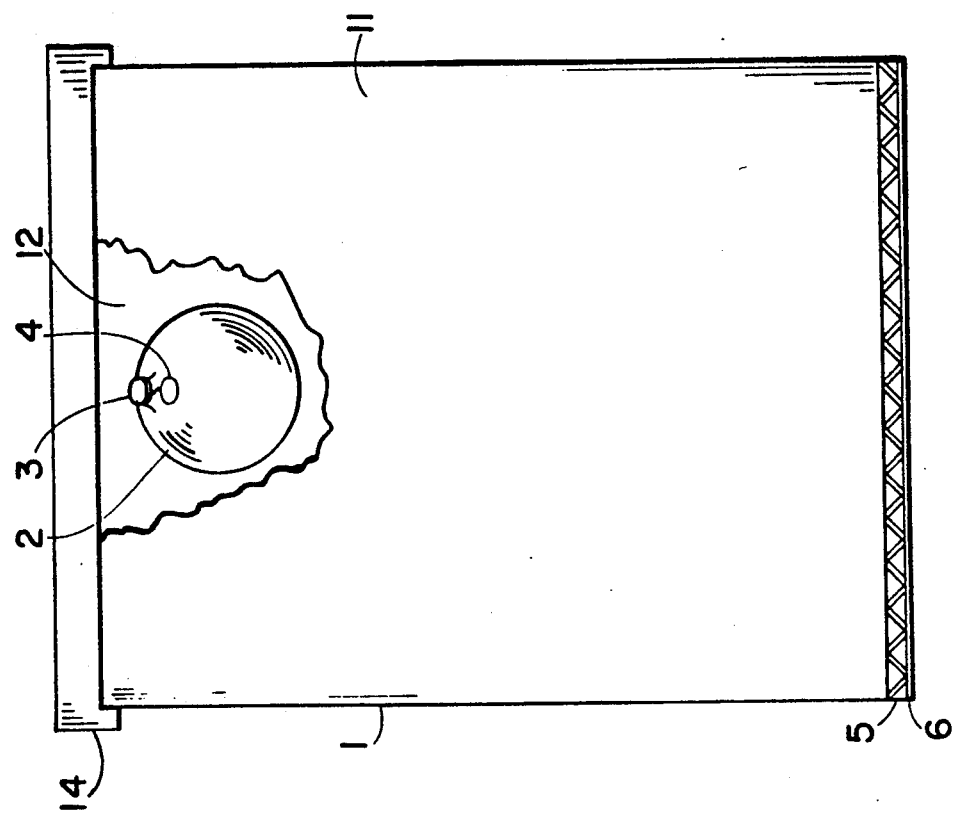
FIG. 2 illustrates where the sharps container will be positioned on the master barrier container.

FIG. 2 illustrates the master barrier container 1 with the sharps container 2 attached by ultrasonic weld 13 (shown in FIG. 1). The sharps container 2 is ultrasonically welded to the back wall 12 of the master barrier container 1.

The master barrier container 1 has a closure system on it comprised of a length of self adhesive tape 14 attached to the back wall 12 of the master barrier container 1. When the master barrier container 1 is filled to recommended levels. Tape 14 is folded over and attached to the front wall 11 of the master barrier container 1. Also a very important part of the master barrier container 1 is the seal 5, a fail proof seal, and below the seal 5 is a skirt 6. Seal 5 comprises a pair of straight, parallel spaced apart transverse seal members and a plurality of angle members extending at acute angles between the transverse members to form triangular areas along the seal.

The support holder/stand 7 shown in FIG. 3 is a very important part of the invention. For mobility, there are casters 10 below the base 9 of the support holder/stand 7 (shown in FIG. 4 and 5). Also shown in FIGS. 3 are the side support rails 15 for the support of the master barrier container 1. The back support 8 is for the back of the sharps container 2 and the back of the rear well which carries the sharps container, to rest against. The base 9 of the support holder/stand 7 houses the casters 10 and serves as the waste support to keep the stream off of the master barrier container's 1, seal 5.

Figure 5:
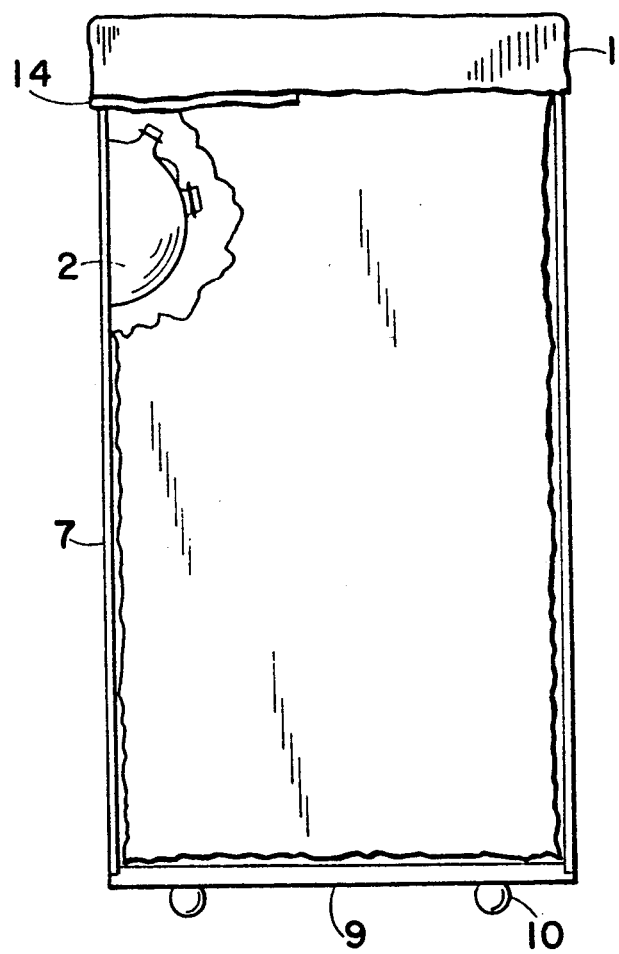
FIG. 5 is a side view of the system.

FIGS. 4 and 5 illustrate the container system. As shown, the support holder/stand 7, supports the master barrier container 1 with the sharps container 2 ultrasonically welded 13 to the inside of the back wall 12 of the master barrier container 1. The invention thus provides a safer means for disposing of and containing infectious medical wastes, sharps or non sharps.

I claim:

1. A single mobile system for containing and disposing of medical sharps and infectious waste comprising:
a master barrier container having an interior surface, said container being adapted to contain non-sharp medical waste, said barrier container having an open top;
a semirigid sharps container adapted to contain sharp medical waste and having a bulbous front wall and a rear wall, said sharps container being fixed to said interior surface of the master barrier container at said rear wall of said sharps container, said sharps container having an opening for receiving said sharp medical waste adjacent said open top of said master barrier container and having a closure adapted to lock closed said opening to close said sharp medical waste in said sharps container; and
means for closing said open top of said master barrier container with said sharps container therein.

2. A system according to claim 1 wherein said master barrier container comprises a plastic tube having a front wall and a rear wall, said sharps container being fixed to said interior surface of said rear wall of said master barrier container, and a seal between said front and rear walls, at a lower end of said tube, said seal comprising a pair of parallel spaced apart straight transverse seal members and a plurality of angle members extending at acute angles between said transverse members and forming a plurality of triangles along said seal.

3. A system according to claim 2, wherein said bulbous front wall of said sharps container is substantially hemispherical and said rear wall of said sharps container being substantially flat.

4. A system according to claim 2 including a mobile support stand adapted to hold said master barrier container with said sharps container therein, said stand comprising a frame for said master barrier container, a base attached to said frame and caster means connected to said base for movement of said mobile support stand.

5. A single mobile system for containing and disposing of medical sharps and infectious waste comprising:
 a master barrier container having an interior surface, said container being adapted to contain non-sharp medical waste, said barrier container having an open top including an open top margin, self-adhesive tape being partially secured to said top margin and being adapted to close said barrier container;
 a semirigid sharps container adapted to contain sharp medical waste, said sharps container being ultrasonically welded to said interior surface of the master barrier container, said sharps container having an opening for receiving said sharp medical waste and having a closure adapted to lock closed said opening to close said sharp medical waste in said sharps container; and
 a mobile support stand adapted to hold said master barrier container with said sharps container, said stand having casters for transporting said stand thereon, said stand including U-shaped stainless steel tubing structure adapted to laterally support said master barrier container.

6. A system according to claim 5 wherein the master barrier container comprises a plastic tube having a front wall, a rear wall and a lower end, said sharps container being ultrasonically welded to said interior surface at said rear wall, and a leak-proof seal at the lower end of said master barrier container, between said and rear walls thereof.

7. A system according to claim 5 wherein said semirigid sharps container has a bulbous front wall and a flat rear wall, said rear wall being welded to said interior surface of said master barrier container.

* * * * *